United States Patent [19]

Yoshida et al.

[11] Patent Number: 5,380,912
[45] Date of Patent: Jan. 10, 1995

[54] ω-HYDROXY-(ω-3)-KETONITRILE

[75] Inventors: Hiroshi Yoshida; Noboru Kakeya; Masanori Kashiwagi, all of Ube, Japan

[73] Assignees: Ube Industries, Ltd., Ube; Soda Aromatic Co., Ltd., Tokyo, both of Japan

[21] Appl. No.: 221,096

[22] Filed: Mar. 31, 1994

Related U.S. Application Data

[62] Division of Ser. No. 20,296, Feb. 19, 1993.

[51] Int. Cl.$^6$ .................. C07C 255/17; C07C 255/12
[52] U.S. Cl. ...................... 558/440; 554/148; 554/154; 554/213; 558/310; 562/579
[58] Field of Search ......................... 558/440

[56] References Cited

U.S. PATENT DOCUMENTS 5,023,351 6/1991 Yoshida et al. .................. 549/321
5,099,036 3/1992 Yoshida et al. .................. 549/321

FOREIGN PATENT DOCUMENTS 0402063 12/1990 European Pat. Off. .

OTHER PUBLICATIONS

Osamu Okuda, Hirokawa Shoten, "Perfume Chemical Comprehensive 2", Feb. 8, 1968, p. 1211.
Osamu Okuda, Hirokawa Shoten, "Perfume Chemical Comprehensive 3", Mar. 13, 1979, pp. 172–174 and 176–177.
Chemical Abstracts, vol. 100, (1984), abstract No. 51058r, L. I. Zakharkin et al.
The Merck Index, 11th Ed., (1989), p. 754.
Kagakudaijiten (Encyclopedia Chemica), pp. 433–434.
Toshio Yokota, "Hydrazine, Properties and Its Application", Jijinshokan, Japan, (1968), pp. 33–39 and partial English language translation.
Yoshida, et al.; C.A. 119:138767n, (1993).

Primary Examiner—Joseph Paul Brust
Attorney, Agent, or Firm—Frishauf, Holtz, Goodman & Woodward

[57] ABSTRACT

ω-Hydroxy-(ω-3)-ketonitrile of the formula $NC(CH_2)_n-CO-(CH_2)_3OH$ wherein n is an integer of 7 to 11.

2 Claims, No Drawings

ω-HYDROXY-(ω-3)-KETONITRILE

This application is a division of application Ser. No. 08/020,296, filed Feb. 19, 1993.

BACKGROUND OF THE INVENTION

This invention relates to an ω-hydroxy-(ω-3)-ketonitrile which is important as a synthetic intermediate or starting material for preparing various compounds, particularly important for preparing an ω-hydroxy fatty acid which is an important intermediate of macrocyclic lactone type perfumes, and a method for producing an ω-hydroxy fatty acid using the same.

There have been known many methods for producing an ω-hydroxy fatty acid which is an important intermediate of macrocyclic lactone type perfumes. Typical examples thereof are introduced in "Perfume Chemical Comprehensive 2", by Osamu Okuda, Hirokawa Shoten, p. 1211 and "Perfume Chemical Comprehensive 3", by Osamu Okuda, Hirokawa Shoten, p.p. 172–174 and 176–177.

The above methods include several drawbacks that these have many steps and are troublesome in handling, expensive agents or agents accompanied by dangers in handling are often required, and also the yield is poor.

The present inventors have studied about a method for preparing ω-hydroxy fatty acid which can solve the problems of the prior art as mentioned above and proposed in Japanese Provisional Patent Publications No. 11036/1991 and No. 11046/1991 (which corresponds to U.S. Pat. Nos. 5,023,351 and 5,099,036 or EP-A-402 063) that an α-(ω-cyanoalkanoyl)-γ-butyrolactone (II) is reacted in an aqueous solution in the presence of 2 to 20 mole of an alkali metal hydroxide per mole of said butyrolactone to obtain an ω-hydroxy-(ω-3)-keto fatty acid (III) and then the acid is reacted with hydrazine to prepare an ω-hydroxy fatty acid (IV). However, in this method, it is difficult to separate the intermediate (III) since it is water-soluble.

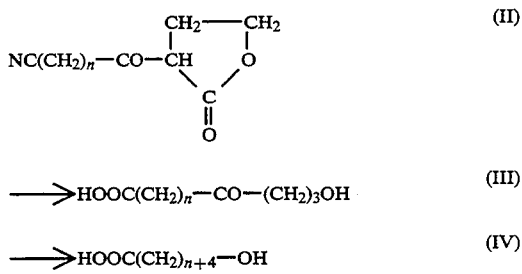

wherein n is an integer of 7 to 11.

SUMMARY OF THE INVENTION

An object of the present invention is to provide a novel method for preparing an ω-hydroxy fatty acid which solves the problems as mentioned above.

The present inventors have further studied about a method for industrially preparing an ω-hydroxy fatty acid advantageously and have found that an ω-hydroxy fatty acid (IV) can be prepared by using a novel compound ω-hydroxy-(ω-3)-ketonitrile (I) as an intermediate whereby the above problems can be solved to accomplish the present invention.

That is, the present invention relates to a novel compound ω-hydroxy-(ω-3)-ketonitrile represented by the following formula (I) which is an important synthetic intermediate for preparing an ω-hydroxy fatty acid.

$$NC(CH_2)_n-CO-(CH_2)_3OH \qquad (I)$$

wherein n is an integer of 7 to 11.

The above compound can be obtained with high yield by reacting an α-(ω-cyanoalkanoyl)-γ-butyrolactone represented by the following formula (II):

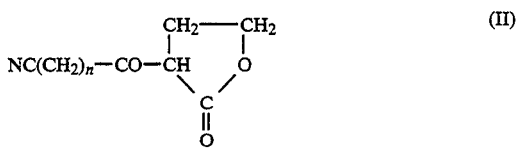

wherein n has the same meaning as defined above, in the presence of 1 to less than 2 mole of an alkali metal hydroxide per mole of said butyrolactone in an aqueous medium.

Further, the method for preparing an ω-hydroxy fatty acid according to the present invention comprises reacting the resulting ω-hydroxy-(ω-3)-ketonitrile (I) with hydrazine in an aqueous solution of an alkali metal hydroxide to obtain an ω-hydroxy fatty acid (IV) easily with high yield.

DESCRIPTION OF THE PREFERRED EMBODIMENT

The method of the present invention can be shown by the following reaction scheme.

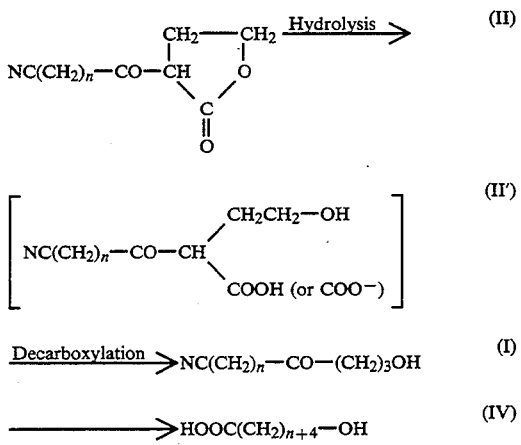

wherein n (First step) has the same meaning as defined above.

ω-Hydroxy-(ω-3)-ketonitrile (I) which is an intermediate of the present invention is water-insoluble and can be easily separated from a reaction mixture. Examples thereof include 12-hydroxy-9-ketododecanonitrile, 13-hydroxy-10-ketotridecanonitrile, 14-hydroxy-11-ketotetradecanonitrile, 15-hydroxy-12-ketopentadecanonitrile, and 16-hydroxy-13-ketohexadecanonitrile.

α-(ω-Cyanoalkanoyl)-γ-butyrolactone (II) which is the starting material of the method of the present invention can be prepared according to the method described in Japanese Provisional Patent Publication No. 11046/1991. Examples thereof include α-(8-cyanooctanoyl)-γ-butyrolactone, α-(9-cyanononanoyl)-γ-butyrolactone, α-(10-cyanodecanoyl)-γ-butyrolactone, α-(11-cyanoundecanoyl)-γ-butyrolactone and α-(12-cyanododecanoyl)-γ-butyrolactone.

The alkali metal hydroxide may include lithium hydroxide, sodium hydroxide and potassium hydroxide, but sodium hydroxide and potassium hydroxide are preferably used. These alkali metal hydroxides may be used in combination of two or more. An amount of the alkali metal hydroxide may be in the range of 1 to less than 2 mole, preferably 1.2 to 1.8 mole per mole of α-(ω-cyanoalkanoyl)-γ-butyrolactone (II). If the amount of the alkali metal hydroxide is less than the lower limit, the reaction does not proceed sufficiently and the starting lactone remains unreacted, while if it exceeds the upper limit, amounts of by-products increase whereby the yield is lowered.

An amount of water as the reaction solvent is preferably in the range of 3 to 20 parts by weight based on 1 part by weight of the alkali metal hydroxide. The reaction temperature is in the range of room temperature to 130° C., preferably 60° to 110° C. Also, the reaction may be carried out under atmospheric condition or under pressure of 10 kg/cm$^2$ or less. The reaction time may be optionally selected depending on the reaction temperature and a starting material to be charged, but usually around 0.1 to 3 hours, preferably 0.5 to 2 hours. The reaction may be carried out by either a batch system or a continuous system.

Separation and purification of the prepared intermediate (I) may be carried out by a unit operation which is itself known in the art, but the compound (I) is water-insoluble so that it can be easily separated by extraction with a solvent such as toluene, etc., or by filtration after cooling and solidifying a reaction mixture.

In the first step, the cyano group of the compound (I) is not hydrolyzed and the lactone portion alone is hydrolyzed to give a reaction intermediate (II') and subsequently led to ω-hydroxy-(ω-3)-ketonitrile (I) by decarboxylation.

(Second step)

The second step can be carried out as follows. That is, ω-hydroxy-(ω-3)-ketonitrile (I) obtained in the first step is reacted with hydrazine (NH$_2$NH$_2$) in an aqueous solution or a mixed solution of a water-soluble organic solvent and water of the alkali metal hydroxide under heating as in the first step. As the reaction solvent, a mixed solution of water and at least one glycol selected from the group consisting of ethylene glycol, diethylene glycol and triethylene glycol is preferred, and an amount of the mixed solution is preferably 1 to 10 parts by weight of the glycol and 5 to 30 parts by weight of water based on 1 part by weight of the alkali metal hydroxide. An amount of the alkali metal hydroxide is preferably 1 to 3 mole equivalent based on ω-hydroxy-(ω-3)-ketonitrile (I). An amount of the hydrazine is 1 to 3 mole equivalent. These amounts of the alkali metal hydroxide, hydrazine and the glycol are less than those of the case where ω-hydroxy fatty acid (IV) is prepared from ω-hydroxy-(ω-3)-keto fatty acid (III), and ω-hydroxy fatty acid (IV) can be obtained with a high yield.

The reaction mechanism of the second step is that ω-hydroxy-(ω-3)-ketonitrile (I) and hydrazine are firstly reacted to form hydrazone, and after CN group is hydrolyzed to COOH group by the alkali metal hydroxide, hydrazone is converted into —CH$_2$— group. Or else, hydrazone is formed and after hydrazone is converted into —CH$_2$— group, CN group is hydrolyzed to COOH group by the alkali metal hydroxide.

The method of the present invention and the method of the above Japanese Provisional Patent Publication No. 11036/1991 or No. 11046/1991 are common in using α-(ω-cyanoalkanoyl)-γ-butyrolactone (II) as a starting material and obtaining ω-hydroxy fatty acid (IV). However, the method of the present invention passes through ω-hydroxy-(ω-3)-ketonitrile (I) which is novel as an intermediate, and has excellent effect as compared with the method of Japanese Provisional Patent Publication No. 11036/1991 or No. 11046/1991 which passes through ω-hydroxy-(ω-3)-keto fatty acid (III) as shown in the following Table 1. That is, the intermediate (I) of the present invention is water-insoluble so that separation thereof is extremely easy and the method of the present invention uses the alkali metal hydroxide with less amounts and the reaction time can be shortened. Further, according to the method of the present invention, the intermediate (I) and the desired compound (IV) can be prepared with high yields, respectively.

TABLE 1

| Intermediate | Compound (III)* | Compound (I) |
|---|---|---|
| (First step) | | |
| Alkali metal hydroxide (mole) | 2 to 20 | 1 to less than 2 |
| Water (parts by weight per 1 part by weight of alkali metal hydroxide) | 3 to 30 | 3 to 20 |
| Reaction temperature (°C.) | Room temperature to 130 | Room temperature to 130 |
| Reaction time (hour) | 1 to 20 | 0.1 to 3 |
| Yield (%) | 90 to 96 | 96 |
| Solubility of product | water-soluble | water-insoluble |
| (Second step) | | |
| Alkali metal hydroxide (mole) | 2.99 | 1.48 |
| Hydrazine (mole) | 2.31 | 1.95 |
| Diethylene glycol (ml) | 1359 | 255 |
| 6N-HCl (ml) | 815 | 400 |
| Yield (%) | 85 | 95 |

*See Japanese Provisional Patent Publication No. 11036/-1991 or No. 1104/1991.

EXAMPLES

The present invention is described in more detail by referring to the following Examples.

Example 1

In a flask were charged 0.279 g (1.00 mmole) of α-(11-cyanododecanoyl)-γ-butyrolactone, 0.068 g (1.70 mmole) of sodium hydroxide and 0.918 g of water and the mixture was refluxed (at about 100° C.) under heating for one hour. After the completion of the reaction, the reaction mixture was extracted twice with 70 ml of toluene. The combined extracts were washed twice with 20 ml of a saturated saline solution, dried over anhydrous sodium sulfate and evaporated to dryness to obtain a white solid. The resulting white solid was purified with use of a silica gel column by using n-hexane : ethyl acetate (2:3, volume ratio) as a developer to obtain 0.243 g (0.96 mole, yield: 96%) of a white solid.

The results of analysis of the white solid are shown below.

(1) m.p. 43° to 45° C.
(2) elemental analysis (in terms of $C_{15}H_{27}NO_2$)

| | C | H | N |
|---|---|---|---|
| Calculated (%) | 71.10 | 10.74 | 5.53 |

|  | C | H | N |
|---|---|---|---|
| Found (%) | 70.56 | 10.90 | 5.40 |

(3) IR (KBr, cm$^{-1}$) 3360, 2250, 1700, 1070.
(4) MS (m/e, CI) 236 (M$^+$ −17)
(5) $^1$H-NMR (CDCl$_3$, δ (ppm)) 1.20~1.37 (10H, broad), 1.37~1.50 (2H, m), 1.50~1.72 (4H, m), 1.83 (2H, qu), 2.05 (1H, s), 2.32 (2H, t), 2.42 (2H, t), 2.56 (2H, t), 3.63 (2H, t).

From the above respective analysis results, it was confirmed that the product was 15-hydroxy-12-ketopentadecanonitrile.

Example 2

Preparation example of 15-hydroxypentadecanoic acid

In a flask were charged 0.507 g (2.0 mmole) of 15-hydroxy-12-ketopentadecanonitrile, 0.170 g (2.96 mmole) of 85% by weight potassium hydroxide, 0.17 g (3.9 mmole) of 85% hydrated hydrazine, 1.52 g of water and 0.51 ml of diethylene glycol and the mixture was mixed and refluxed under heating for 5 hours. Subsequently, while evaporating the produced light boiling components such as water to the outside of the system, the internal temperature was elevated to 195° to 205° C., and the mixture was continued to reflux at the same temperature for 4 hours. After completion of the reaction, the reaction mixture was cooled, diluted by addition of 3 ml of water and added with 0.8 ml of 6N-HCl, followed by collection of the precipitated pale brown solid by filtration. The solid was recrystallized from benzene to obtain 0.491 g (1.9 mmole, Yield: 95%, Purity: 99% or more) of a white crystal. When the white crystal was analyzed, it was confirmed that the product was 15-hydroxypentadecanoic acid.

We claim:

1. ω-Hydroxy-(ω-3)-ketonitrile represented by the following formula (I):

$$NC(CH_2)_n-CO-(CH_2)_3OH \quad (I)$$

wherein n is an integer of 7 to 11.

2. ω-Hydroxy-(ω-3)-ketonitrile according to claim 1, wherein said compound is 15-hydroxy-12-ketopentadecanonitrile.

* * * * *